United States Patent
Tsukuda

(10) Patent No.: US 9,523,123 B2
(45) Date of Patent: Dec. 20, 2016

(54) DNA DETECTION METHOD AND DNA DETECTION DEVICE

(71) Applicant: Panasonic Intellectual Property Management Co., Ltd., Osaka (JP)

(72) Inventor: Masahiko Tsukuda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/047,615

(22) Filed: Feb. 18, 2016

(65) Prior Publication Data

US 2016/0257992 A1    Sep. 8, 2016

(30) Foreign Application Priority Data

Mar. 4, 2015 (JP) ................. 2015-042915

(51) Int. Cl.
*C12Q 1/68* (2006.01)

(52) U.S. Cl.
CPC .................... *C12Q 1/686* (2013.01)

(58) Field of Classification Search
CPC ....... C12Q 1/68; C12Q 1/6802; C12Q 1/6806; C12Q 1/6809; C12Q 1/6811; C12Q 1/6813; C12Q 1/6818; C12Q 1/682; C12Q 1/6825; C12Q 1/686; C12Q 1/6853; C12Q 1/6844
See application file for complete search history.

(56) References Cited

U.S. PATENT DOCUMENTS

| | | | |
|---|---|---|---|
| 2008/0038810 A1* | 2/2008 | Pollack | B01L 3/502761 435/283.1 |
| 2008/0314761 A1* | 12/2008 | Herminghaus | B01F 3/0807 205/687 |
| 2009/0217742 A1* | 9/2009 | Chiu | G01N 27/44717 73/61.55 |
| 2011/0053798 A1* | 3/2011 | Hindson | C12Q 1/6844 506/12 |
| 2011/0217736 A1* | 9/2011 | Hindson | C12P 19/34 435/91.2 |
| 2011/0311978 A1* | 12/2011 | Makarewicz, Jr. | B01F 3/0807 435/6.12 |
| 2012/0171683 A1* | 7/2012 | Ness | C12Q 1/6806 435/6.12 |

(Continued)

FOREIGN PATENT DOCUMENTS

| | | |
|---|---|---|
| JP | 6-500021 | 1/1994 |
| JP | 2013-524169 | 6/2013 |

(Continued)

*Primary Examiner* — Shogo Sasaki
(74) *Attorney, Agent, or Firm* — McDermott Will & Emery LLP

(57) ABSTRACT

Disclosed is a DNA detection device that detects a target DNA by detecting fluorescence output from sample droplets flowing through a flow path in a surface of a sensor chip, and that includes a fluorescence detector that detects fluorescence output from sample droplets flowing through the flow path, and a DNA detector that determines a type of fluorescent probe solution contained in each of the sample droplets based on a duration of the detected fluorescence and determines whether or not the sample droplet contains the target DNA based on whether intensity of the fluorescence is higher or lower than a threshold value.

9 Claims, 10 Drawing Sheets

(56) References Cited

U.S. PATENT DOCUMENTS

| | | | | |
|---|---|---|---|---|
| 2012/0190033 A1* | 7/2012 | Ness | ................... | B01L 3/021 |
| | | | | 435/6.12 |
| 2012/0194805 A1* | 8/2012 | Ness | ................... | G01N 21/05 |
| | | | | 356/213 |
| 2012/0219947 A1* | 8/2012 | Yurkovetsky | ......... | B01F 5/0471 |
| | | | | 435/6.11 |
| 2012/0264646 A1* | 10/2012 | Link | ................... | B01F 5/0646 |
| | | | | 506/11 |
| 2012/0309002 A1* | 12/2012 | Link | ................ | C12N 15/1068 |
| | | | | 435/6.11 |
| 2012/0329664 A1* | 12/2012 | Saxonov | ............. | C12Q 1/6851 |
| | | | | 506/9 |
| 2013/0040841 A1* | 2/2013 | Saxonov | ............. | C12Q 1/6851 |
| | | | | 506/9 |
| 2013/0084572 A1* | 4/2013 | Hindson | ........... | G01N 21/6428 |
| | | | | 435/6.12 |
| 2013/0099018 A1* | 4/2013 | Miller | ................ | C12Q 1/6806 |
| | | | | 239/10 |
| 2013/0109575 A1* | 5/2013 | Kleinschmidt | .... | G01N 33/5302 |
| | | | | 506/2 |

FOREIGN PATENT DOCUMENTS

| WO | 92/02638 | 2/1992 |
|---|---|---|
| WO | 2011/120006 | 9/2011 |

\* cited by examiner

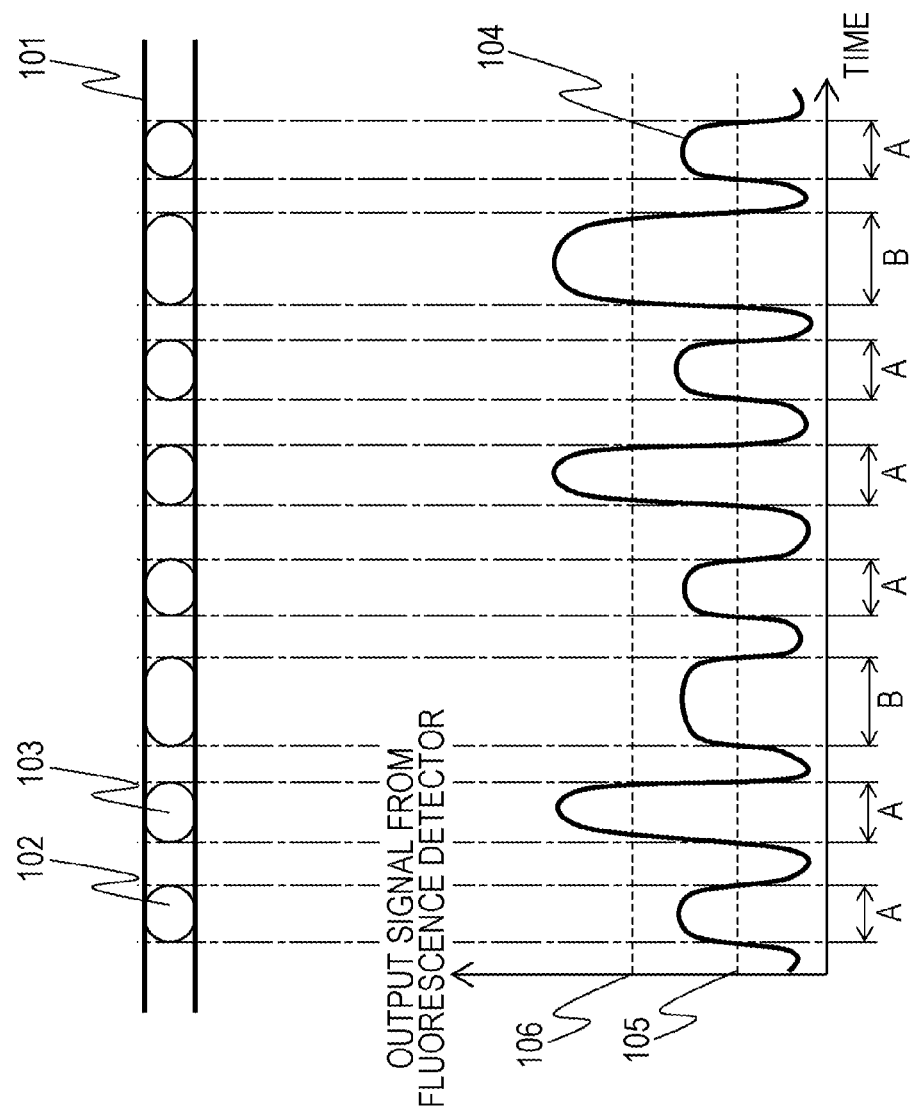

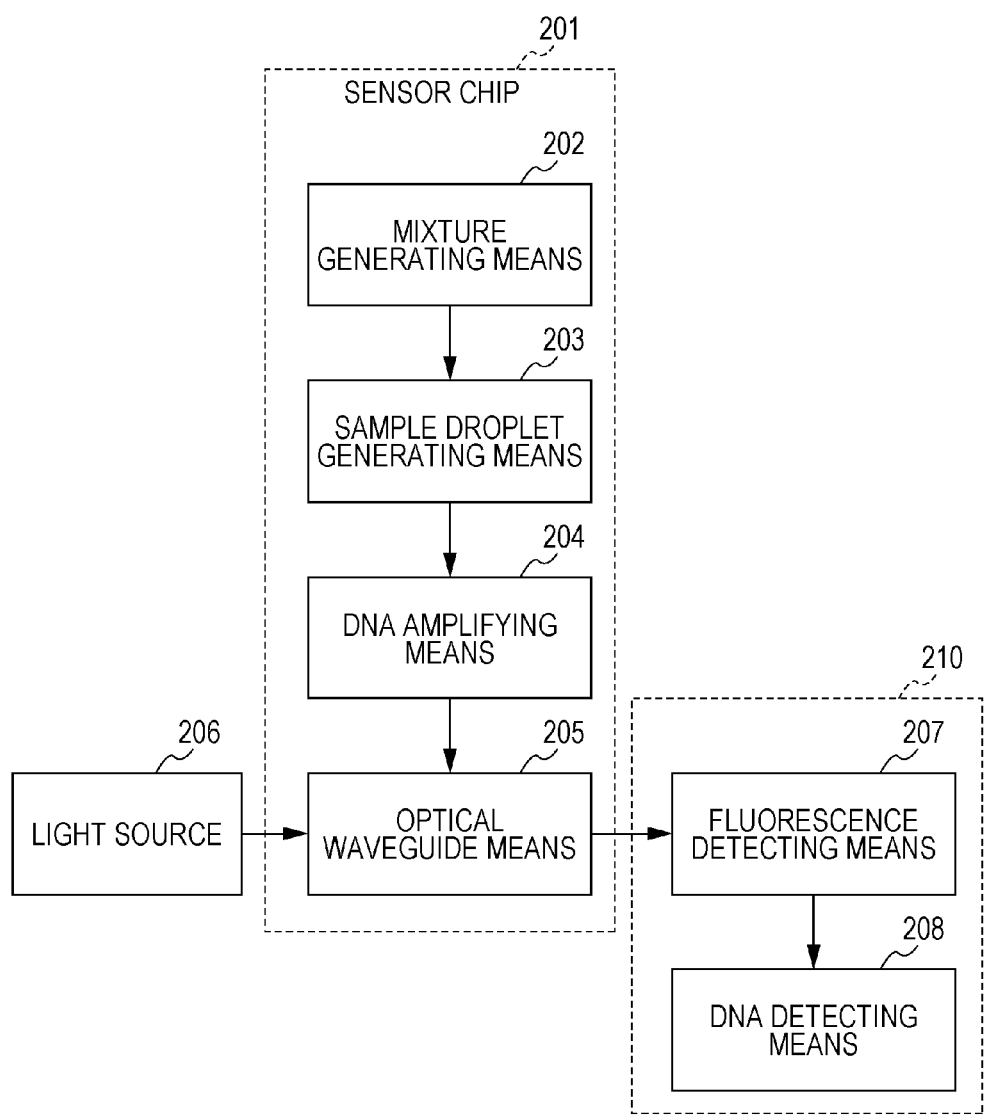

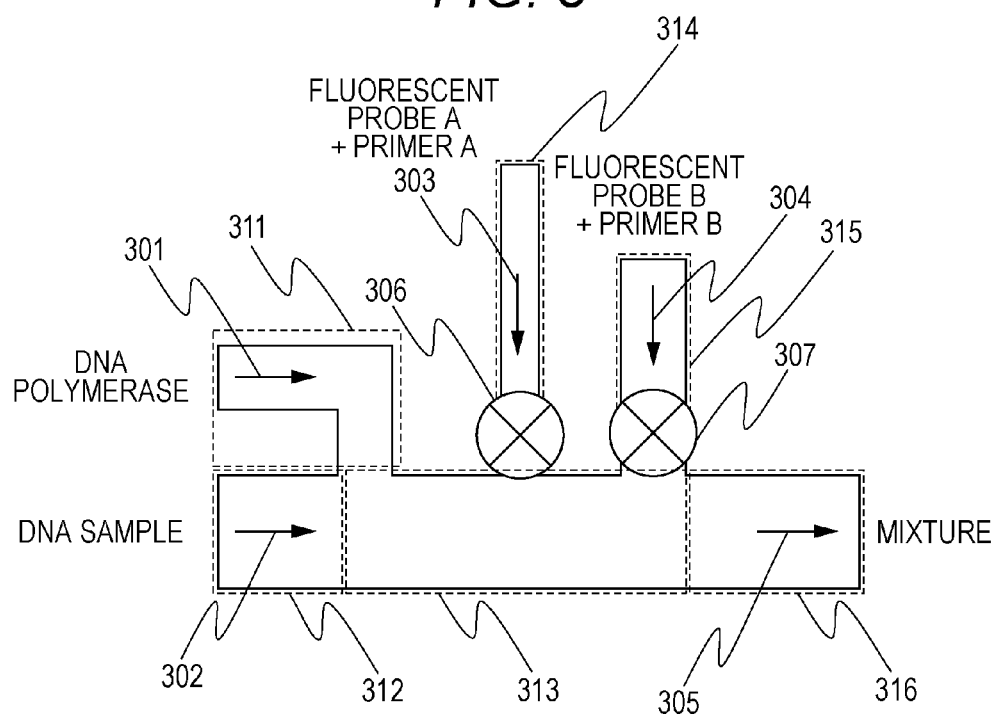
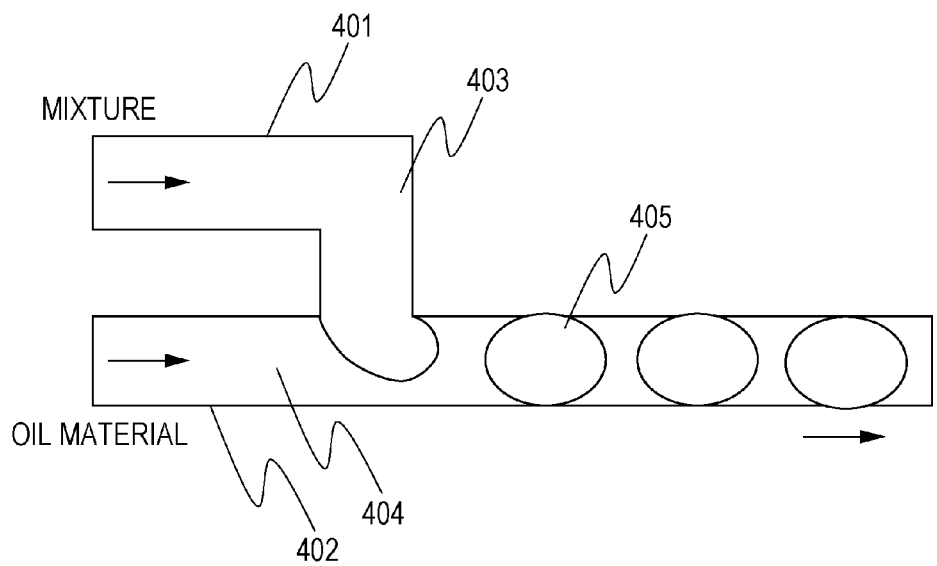

DNA DETECTION METHOD AND DNA DETECTION DEVICE

BACKGROUND

1. Technical Field

The present disclosure relates to a method and a device for detecting a gene (DNA).

2. Description of the Related Art

There is a method in which a desired DNA/RNA fragment of a gene is amplified to an amount necessary for detection by a technique called PCR (Polymerase Chain Reaction) to detect the desired DNA/RNA fragment. Further, a quantitative analysis technique called qPCR (quantitative PCR) is often used as an advanced type of PCR. Such a quantitative gene analysis technique is introduced in a compact reactor or the like provided in a microchannel chip.

Patent Literature 1 discloses a basic method for implementing qPCR for quantitative gene analysis. According to Patent Literature 1, a sample containing a single-stranded DNA is brought into contact with an oligonucleotide (short DNA/RNA sequence) having a sequence complementary to a first region of a target DNA sequence and a labeled oligonucleotide containing a sequence complementary to a second region of the same target DNA sequence. A double-stranded complex mixture is prepared under conditions where hybridization occurs, and the annealed labeled oligonucleotide is cleaved by 5"→3' nuclease activity to liberate a labeled fragment. A method for detecting such a liberated labeled fragment is disclosed. When the labeled oligonucleotide is prepared by labeling with a fluorescent dye and a quencher, fluorescence is not emitted until a labeled fragment is liberated, and fluorescence intensity is increased by repeating the above process. The fluorescence intensity is detected with a photodetector to analyze how much the target DNA sequence of interest is contained. When DNA/RNA sequences of two or more regions need to be detected per sample, labeled oligonucleotides complementary to the different DNA/RNA sequences are prepared by labeling with different fluorescent dyes that emit fluorescence of different wavelengths. Such a difference in fluorescence wavelength makes it possible to separately analyze the DNA/RNA sequences with a photodetector.

Patent Literature 2 discloses one example of a method for implementing a quantitative gene analysis technique. Particularly, Patent Literature 2 discloses a technique for improving a high-throughput assay using an emulsification technique. The emulsification technique is used to generate droplets that function as independent reaction chambers for biochemical reactions, and individual sub-components (e.g., cells, nucleic acids, and proteins) are processed and assayed using the droplets.

Aqueous droplets containing DNA/RNA or the like are suspended in oil to prepare an emulsion in which water is dispersed in oil. This emulsion is stabilized with a surfactant so that coalescence of droplets during heating, cooling, or transport can be reduced or prevented. This makes it possible to perform thermal cycling. For this reason, emulsions are used to perform single-copy amplification of nucleic acid target molecules in droplets using PCR. Among these droplets, those positive for a target can be analyzed based on Poisson statistics to estimate a concentration of the target in a sample. Droplet-based assays use one or more fluorophores as labels in droplets to determine the occurrence of a reaction such as amplification. Droplets are generated and reacted, and then light emitted from each of the droplets is measured, which makes it possible to determine whether or not a target is present in the droplet. When different distinguishable fluorophores are used for different targets, the presence or absence of two or more different targets can be measured in each droplet. In such a case where two or more different targets need to be distinguished, two or more fluorophores, that is, dye materials that emit fluorescence of different wavelengths are often used to distinguish the targets based on their fluorescence wavelengths. Patent Literature 2 discloses a method for distinctively detecting two fluorophores used. The method is achieved by providing different detection systems (including a light source and a detector) for first and second dyes so that the detection system for the first dye and the detection system for the second dye alternately detect droplets when the droplets pass through an examination region of a channel.

CITATION LIST

Patent Literatures

PTL 1: Japanese Patent No. 2,825,976
PTL 2: Japanese Translation of PCT Publication No, 2013-524169

However, when such a conventional system is used to simultaneously detect two or more target DNA/RNA base sequence patterns, fluorescent probes to be bound to the different base sequences need to have different fluorescence wavelengths to separately detect the target sequence patterns. In this case, a detector that detects fluorescence needs to have light sources provided for different fluorescent dyes and detectors provided for different fluorescence wavelengths of the fluorescent dyes. This involves a problem that an optical system that detects fluorescence becomes more complicated as a number of DNA base sequence patterns to be simultaneously detected increases.

SUMMARY

One non-limiting and exemplary embodiment provides a sensor chip that is compact in size and inexpensive and that does not require a more complicated optical system that detects fluorescence even when a number of DNA sequence patterns to be simultaneously detected increases.

In one general aspect, the techniques disclosed here feature a DNA detection method including:

(a) placing a sensor chip in a DNA detection device, wherein the DNA detection device includes:
a PCR processor, a fluorescence detector, and a DNA detector, the sensor chip includes:
a first flow path, a second flow path, a third flow path, a fourth flow path, a fifth flow path, a sixth flow path, a seventh flow path, an eighth flow path, and a ninth flow path, a first end of the first flow path and a first end of the second flow path are connected to a first end of the third flow path, a second end of the third flow path is connected to a first end of the sixth flow path, the fourth flow path and the fifth flow path are connected between the first end and the second end of the third flow path, a second end of the sixth flow path and a first end of the seventh flow path are connected to a first end of the eighth flow path, a second end of the eighth flow path is connected to the PCR processor, and the PCR processor is connected to the ninth flow path;

(b) introducing an aqueous DNA solution and an aqueous DNA polymerase solution into the first flow path and the second flow path, respectively, to pass a first aqueous mixture of the aqueous DNA solution and the aqueous DNA polymerase solution through the third flow path, wherein the aqueous DNA solution contains a target single-stranded DNA;

(c) introducing a first aqueous fluorescent probe solution obtained by mixing a first fluorescent probe with a first primer into the fourth flow path at a first flow rate during flowing of the first aqueous mixture through the third flow path to pass a second aqueous mixture of the first aqueous mixture and the first aqueous fluorescent probe solution through the sixth flow path, wherein the first fluorescent probe complementarily binds to a first single-stranded DNA;

(d) introducing an oil material into the seventh flow path at a second flow rate to pass parts of the second aqueous mixture and parts of the oil material through the eighth flow path, wherein the parts of the second aqueous mixture and the parts of the oil material are arranged alternately along the eighth flow path;

(e) introducing a second aqueous fluorescent probe solution obtained by mixing a second fluorescent probe with a second primer into the fifth flow path at a third flow rate during flowing of the first aqueous mixture through the third flow path to flow a third aqueous mixture of the first aqueous mixture and the second aqueous fluorescent probe solution through the sixth flow path, wherein the second fluorescent probe is different from the first fluorescent probe and complementarily binds to a second single-stranded DNA;

(f) introducing the oil material into the seventh flow path at a fourth flow rate to pass parts of the third aqueous mixture and parts of the oil material through the eighth flow path, wherein the parts of the third aqueous mixture and the parts of the oil material are arranged alternately along the eighth flow path;

(g) processing the parts of the second aqueous mixture and the parts of the third aqueous mixture by PCR with the PCR processor and then passing the parts through the ninth flow path;

(h) detecting, with the fluorescence detector, intensity of fluorescence output from each of the parts of the second aqueous mixture and the parts of the third aqueous mixture flowing through the ninth flow path; and (i) determining, with the DNA detector, whether or not the target single-stranded DNA contains at least one selected from the first single-stranded DNA and the second single-stranded DNA based on the intensity of transmitted light, the first flow rate, the second flow rate, the third flow rate, and the fourth flow rate.

According to the DNA detection method of the present disclosure using a sensor chip, fluorescent dyes that emit fluorescence of a same wavelength can be used for fluorescent probes even when a number of DNA sequence patterns to be simultaneously detected increases, and therefore a DNA can be detected using a compact and inexpensive sensor chip without complicating an optical system for detecting fluorescence.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

It should be noted that general or specific embodiments may be implemented as a system, a method, an integrated circuit, a computer program, a storage medium, or any selective combination thereof.

BRIEF DESCRIPTION OF THE DRAWINGS

FIG. 1 is a schematic diagram showing droplets flowing through a flow path of an optical waveguide means, and optical signals of the droplets detected by a PMT;

FIG. 2 is a block diagram showing structures of a sensor chip and a DNA detection device according to a first exemplary embodiment;

FIG. 3 is a schematic diagram showing one example of a structure of a mixture generating means;

FIG. 4 is a schematic diagram showing one example of a structure of one flow path that generates sample droplets;

DETAILED DESCRIPTION OF THE EMBODIMENT

Figure 5:
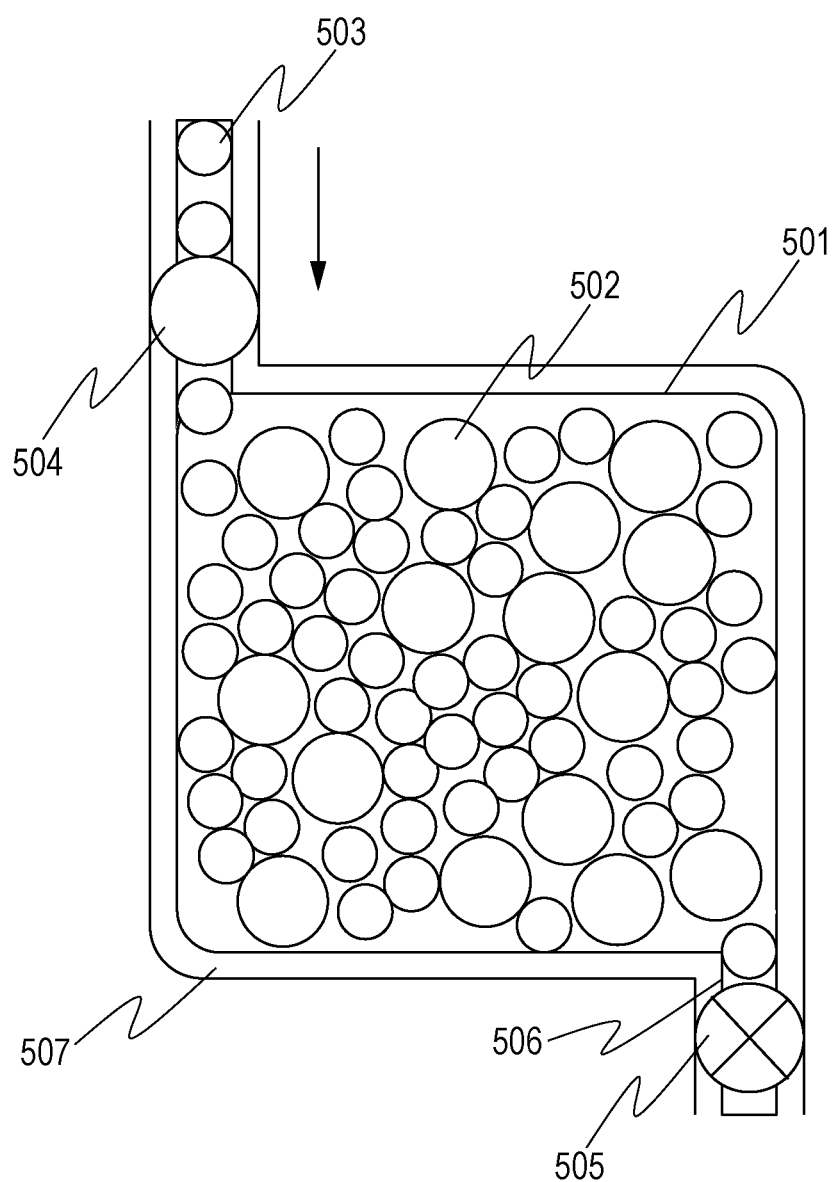
FIG. 5 is a schematic diagram showing one example of a structure of a DNA amplifying means.

First, a gene testing method will be described. A gene is a major factor carrying genetic information of a living thing. In all living things, genetic information is coded in a base sequence of DNA/RNA (nucleic acid) serving as a medium. In recent years, genetic diversity analysis or gene expression analysis has been remarkably developed through improvement in genetic diagnosis technology. Particularly, a relationship between genetic information and diseases has attracted attention in a medical field. For example, treatment or medication tailored to each individual patient (tailor-made medicine) has become possible by analyzing information about individual genes associated with diseases (DNA/RNA sequences of specific regions). In tailor-made medicine, in-situ diagnosis is most preferred, and therefore a quick and simple diagnostic method that provides high quality POCT (Point of Care Testing) is required. For this reason, there has been a strong demand for development of a device that can quickly and simply extract DNA/RNA of a gene to be analyzed from a collected sample such as blood, amplify the extracted DNA/RNA, and detect information about a sequence of the DNA/RNA or an amount of the DNA/RNA.

As one of means that meet such a demand, devices called μTAS (μ Total Analysis Systems) or LoC (Lab on Chip) have attracted attention in recent years. The μTas or LoC is a device having a substrate in which microchannels or ports are provided as micrometer-order microstructures to perform various operations such as mixing of substances, extraction, purification, chemical reaction, and analysis in the microstructures. Some μTASs or LoCs have already been put to practical use. Such a device performs various operations in microstructures, and therefore has advantages that an amount of a sample or reagent used is much smaller, analysis time is shorter, and sensitivity is higher as compared to a same type of device of a regular size used in so-called specialized laboratories or analysis organizations. Further, such a device can be configured to have a small and portable size, and therefore can be used not only in specialized laboratories but also for in-situ analysis. Structures that are produced for such a purpose, that have microstructures such as microchannels or ports provided in a substrate, and that integrate various functions are collectively called "microchannel chips (sensor chips)" or "microfluidic devices."

In order to analyze a gene contained in a sample in a short time using a microchannel chip, it is desired that functions of extraction, amplification, and detection of DNA/RNA of a gene are integrated in the chip. Particularly, in order to obtain more information in a short time, it is necessary to detect two or more samples at a time in one chip or to amplify and detect DNA/RNA sequences of two or more regions per sample (multiplex amplification and detection). Further, depending on intended use, it is necessary to analyze an amount of a desired gene (quantitative analysis).

Hereinbelow, a sensor chip and a DNA detection device according to an exemplary embodiment of the present disclosure will be described with reference to accompanying drawings.

First Exemplary Embodiment

Sensor chip 201 and DNA detection device 210 according to a first exemplary embodiment will be described with reference to accompanying drawings. FIG. 2 is a block diagram showing structures of sensor chip 201 and DNA detection device 210 according to the first exemplary embodiment.

<Sensor Chip>

Sensor chip 201 will be described. Sensor chip 201 is a substrate having a surface in which a recess is formed. A material of the substrate is, for example, silicon. The recess corresponds to a flow path (groove). For example, the flow path has a width and a depth that are of the order of several hundred micrometers. This flow path connects mixture generating means 202, one flow path 203 that generates sample droplets, DNA amplifying means 204, and optical waveguide means 205 to one another. Hereinbelow, each of the components of sensor chip 201 will be described.

<Mixture Generating Means>

FIG. 3 is a schematic diagram showing one example of a structure of mixture generating means 202. Mixture generating means 202 shown in FIG. 3 includes two or more flow paths. Valves 306 and 307 are provided at joints between the flow paths of mixture generating means 202.

Mixture generating means 202 shown in FIG. 3 has first flow path 311, second flow path 312, third flow path 313, fourth flow path 314, fifth flow path 315, and sixth flow path 316. DNA polymerase 301 flows through first flow path 311. DNA-containing sample 302 flows through second flow path 312. A DNA mixture obtained by mixing DNA polymerase 301 with DNA-containing sample 302 flows through third flow path 313. First fluorescent probe 303 and first primer 303 flow through fourth flow path 314. Second fluorescent probe 304 and second primer 304 flow through fifth flow path 315. A mixture obtained by mixing the DNA mixture, first fluorescent probe 303, and first primer 303 or a mixture obtained by mixing the DNA mixture, second fluorescent probe 304, and second primer 304 flows through sixth flow path 316. Each of first flow path 311, second flow path 312, fourth flow path 314, and fifth flow path 315 may have a pump for introducing DNA polymerase 301, DNA-containing sample 302, first fluorescent probe 303 and first primer 303, or second fluorescent probe 304 and second primer 304, respectively. When two materials are contained as shown in FIG. 3, their respective liquids are supplied to the flow path one by one so as not to be mixed together. In FIG. 3, when first fluorescent probe 303 and first primer 303 are supplied to the flow path, valve 307 of the flow path through which second fluorescent probe 304 and second primer 304 are supplied is closed to prevent mixing with second fluorescent probe 304 and second primer 304.

Further, when second fluorescent probe 304 and second primer 304 are supplied to the flow path, valve 306 is closed and valve 307 is opened to prevent the first fluorescent probe and the first primer from being supplied to the flow path. As described above, when two or more combinations of a fluorescent probe and a primer are used, different flow paths are provided for the different combinations of a fluorescent probe and a primer, and each of the flow paths and third flow path 313 are connected to each other via a valve. The valves each provided between the flow path and third flow path 313 are controlled so that only any one of the valves is opened. In this way, the two or more different combinations of a fluorescent probe and a primer are prevented from being mixed together. It is to be noted that mixture generating means 202 has been described above with reference to a case where mixture generating means 202 has such a structure as shown in FIG. 3, but effects of the present disclosure are not affected at all even when mixture generating means 202 has a different flow path configuration as long as different liquids each containing a fluorescent probe and a primer can be separately supplied. For example, a flow path that supplies first fluorescent probe and first primer 303 and a flow path that supplies second fluorescent probe and second primer 304 may be provided so as to be opposed to each other across a flow path through which DNA-containing sample 302 flows.

<One Flow Path that Generates Sample Droplets>

FIG. 4 is a schematic diagram showing one example of a structure of one flow path that generates sample droplets. As shown in FIG. 4 by way of example, sixth flow path 401 for flowing mixture 403 generated by mixture generating means 202 and seventh flow path 402 for flowing oil material 404 are connected to each other in a T shape so that mixture 403 and oil material 404 join together in one eighth flow path. Mixture 403 and oil material 404 join together at a T-shaped joint, but are not mixed together. Therefore, the mixture is divided by oil material 404 into small droplets 405 in one flow path (eighth flow path). As long as a flow rate of the mixture per unit time and a flow rate of the oil material per unit time are stable, droplets of almost a same size are continuously formed. A pump that introduces the oil material may be provided in seventh flow path 402.

For example, when a predetermined flow rate per unit time is achieved in each of first flow path 311, second flow path 312, fourth flow path 314, fifth flow path 315, and seventh flow path 402 by the pump provided in each of the flow paths, droplets of a predetermined size are formed.

The one flow path that generates sample droplets has been described above with reference to a case where the one flow path has a structure in which flow paths are connected to each other in a T shape as shown in FIG. 4. However, a structure of the one flow path that generates sample droplets is not limited thereto, and may be one in which the mixture and the oil material are joined together by supplying the oil material from both sides of a flow path for supplying the mixture. That is, as long as droplets of the mixture are formed by collision between the mixture and the oil material, effects of the present disclosure are not affected even when the one flow path that generates sample droplets has a different flow path configuration.

<DNA Amplifying Means>

FIG. 5 is a schematic diagram showing one example of a structure of DNA amplifying means 204. DNA amplifying means 204 includes chamber 501 that can hold the droplets. Inlet 503 of chamber 501 is opened and closed by valve 504, and outlet 506 of chamber 501 is opened and closed by valve 505. When the droplets are introduced into chamber 501, both inlet 503 and outlet 506 are opened until an inside of chamber 501 is filled with the droplets, and then inlet 503 and outlet 506 are closed by valves 504 and 505. In chamber 501, DNA amplification is performed by PCR (Polymerase Chain Reaction). This processing is also referred to as PCR processing. One example of DNA amplifying means 204 includes a chamber and a heater. Chamber 501 is positioned between the eighth flow path and a ninth flow path. DNA amplifying means 204 is also referred to as a PCR processor.

Figure 10A:
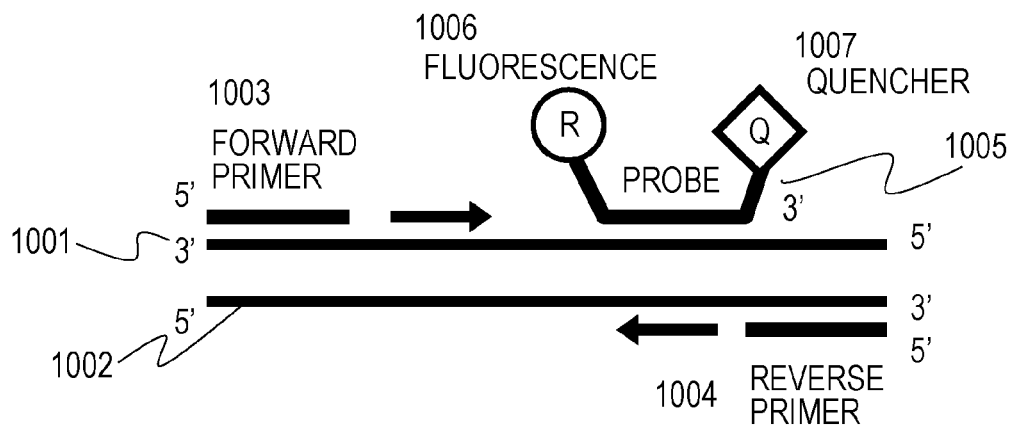
FIG. 10A is a schematic diagram showing each step of PCR using TaqMan probe.
Figure 10B:
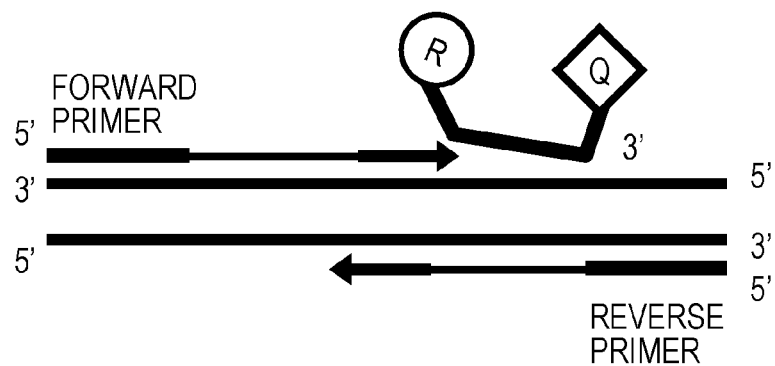
FIG. 10B is a schematic diagram showing each step of PCR using TaqMan probe.
Figure 10C:
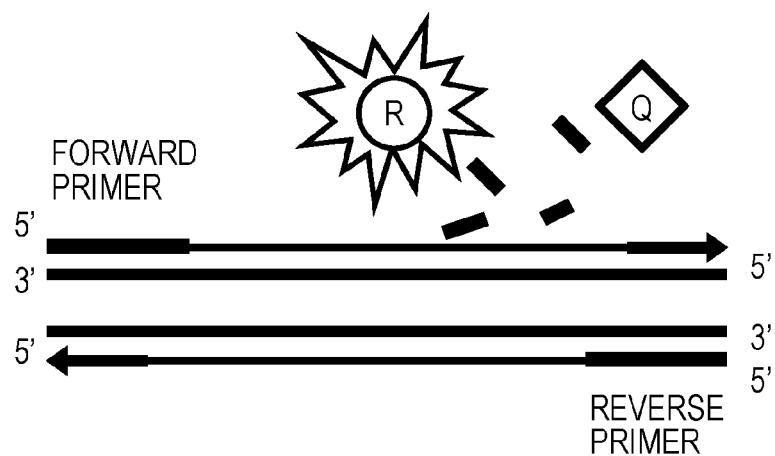
FIG. 10C is a schematic diagram showing each step of PCR using TaqMan probe.

FIGS. 10A to 10C are each a schematic diagram showing each step of PCR using TagMan probe as a fluorescent probe.

As shown in FIG. 10A, a DNA has a double-stranded structure in which two complementary sequence strands (1001, 1002) bind together. When heated to a certain temperature, double-stranded DNA is separated into single-stranded DNAs (1001, 1002). For example, when single-stranded DNA 1001 is a target DNA, a sample containing the single-stranded DNA is brought into contact with primer (1003) having a sequence complementary to a first region of sequence strand of target DNA 1001 and fluorescent probe (oligonucleotide labeled with a fluorescent dye, 1005) containing a sequence complementary to a second region of sequence strand of the same target DNA under conditions where hybridization occurs, primer 1003, fluorescent probe 1005, and target DNA 1001 form a double-stranded complex. Further, primer 1004 for single-stranded DNA 1002 that is not a target DNA binds to single-stranded DNA 1002. However, since single-stranded DNA 1002 is not a target DNA, the fluorescent probe does not bind to single-stranded DNA 1002.

Then, as shown in FIG. 10B, when conditions where nuclease activity is activated are created, a DNA polymerase starts to extend a DNA from primer 1003 bound to single-stranded DNA 1001 and from primer 1004 bound to single-stranded DNA 1002.

When DNA extension proceeds as shown in FIG. 10C, fluorescent probe 1005 bound to target DNA 1001 is liberated. Before the liberation of fluorescent probe 1005, fluorescent dye 1006 and quencher 1007 contained in fluorescent probe 1005 are in close proximity to each other, and therefore the fluorescent dye does not emit fluorescence. However, when the fluorescent probe is liberated by DNA extension, a distance between fluorescent dye 1006 and quencher 1007 increases so that fluorescent dye 1006 emits fluorescence.

One fluorescent dye emits fluorescence per target DNA strand in one cycle including a series of these steps. Further, each single-stranded DNA is converted into double-stranded DNA by DNA extension, and therefore the DNA is amplified two-fold. That is, a number of DNA strands amplified increases as a power of 2 as a number of repeats of the cycle increases. Also, a number of times that liberation of the fluorescent dye occurs is a power of 2. Therefore, fluorescence intensity is increased by repeating this cycle.

Depending on a type of primer or fluorescent probe used, a temperature for separating a double-stranded DNA into single-stranded DNAs is often set to about 90° C. a temperature for hybridizing a primer or a fluorescent probe is often set to about 60° C., and a temperature for DNA extension performed by a DNA polymerase when nuclease is activated is often set to about 70° C. That is, DNA amplification by PCR is performed by repeating such a thermal cycle of heating and cooling. DNA amplifying means 204 is required to quickly repeat such a thermal cycle. Therefore, when a substrate made of a material having high thermal conductivity, such as a Si substrate, is used, heat radiation needs to be suppressed by, for example, separating a chamber region from a Si member surrounding the chamber region. In the first exemplary embodiment, as shown in FIG. 5, gap 507 is provided by etching or the like around chamber 501 of DNA amplifying means 204 provided in a Si substrate. Such a structure prevents heat applied to the chamber from being diffused to surroundings of the chamber, and therefore a very quick thermal cycle is achieved.

<DNA Detection Device>

Figure 6:
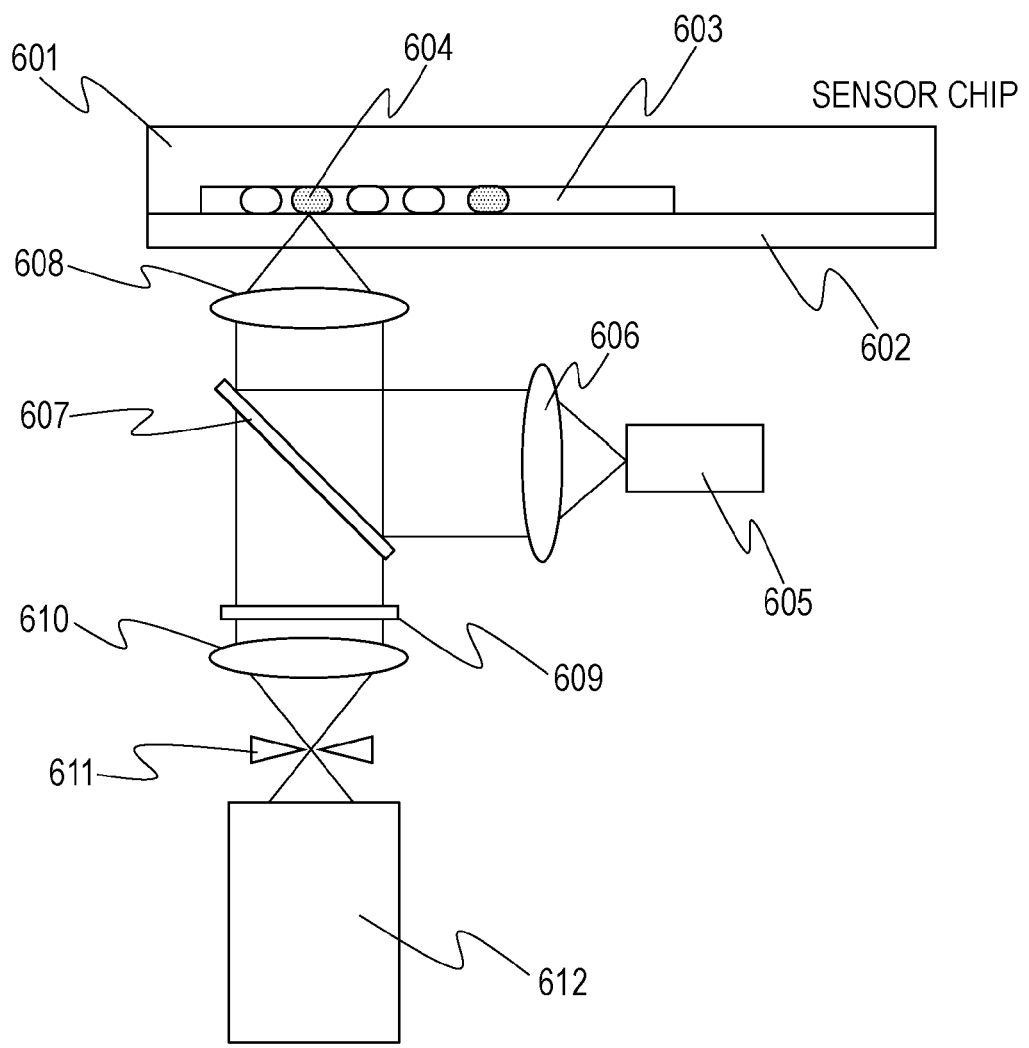
FIG. 6 is a schematic diagram showing one example of a structure of an optical detection system including an area corresponding to the optical waveguide means of the sensor chip and a DNA detection device.

Then, DNA detection device 210 will be described. DNA detection device 210 includes fluorescence detecting means 207 for detecting fluorescence from the sample droplets and DNA detecting means 208 for determining a type of fluorescent probe solution contained in each of the sample droplets based on a duration of detected fluorescence and for determining the presence or absence of a DNA to be detected based on whether the detected fluorescence is higher or lower than a threshold value. It is to be noted that DNA detection device 210 may further include excitation light source 206 for fluorescence detection. FIG. 6 is a schematic diagram showing one example of a structure of an optical detection system including an area corresponding to the optical waveguide means of the sensor chip and DNA detection device 210. Hereinbelow, each of the components of the optical detection system including an area corresponding to the optical waveguide means of the sensor chip and DNA detection device 210 will be described.

<Optical Waveguide Means of Sensor Chip>

The sensor chip is formed by providing a groove having a length of several hundred micrometers in a surface of Si substrate 601 and bonding glass plate 602 onto the surface of Si substrate 601 by, for example, anodic bonding. Bonding glass plate 602 onto the surface of Si substrate 601 allows the groove to serve as flow path 603 through which the droplets flow. Droplets 604 having been subjected to DNA amplification continuously flow in line through flow path 603 at a predetermined constant rate. Droplets 604 need to be irradiated with light for exciting the fluorescent dye, and fluorescence emitted by the irradiation needs to be extracted into the fluorescence detecting means. In the case of the chip having such a structure as described above, light is input and output through a glass surface. In this structure, an optical path from the glass surface to the flow path through which the droplets flow corresponds to the optical waveguide means.

<Light Source>

In order to efficiently excite the fluorescent dye, a laser, an LED, or the like with a wavelength close to a maximum absorption wavelength of absorption spectrum of the dye is used as the light source. Particularly, the optical system is preferably as small and powerful as possible, and the light source is preferably a semiconductor laser or the like. In the first exemplary embodiment, semiconductor laser 605 with a wavelength of 490 nm is used. Laser light emitted from semiconductor laser 605 is changed to parallel light by collimator lens 606 and reflected by dichroic mirror 607.

<Fluorescence Detecting Means>

The dichroic mirror is a mirror that can reflect some wavelengths but transmit others. In the first exemplary embodiment, for example, a dichroic mirror with a cutoff of 505 nm is used. The dichroic mirror reflects light of wavelengths shorter than 505 nm but transmits light of wavelengths longer than 505 nm. Reflected laser light is focused through objective lens 608 onto a position in flow path 603 where each of the droplets passes through. The droplets containing a target DNA contain a large amount of the liberated fluorescent dye, and therefore the fluorescent dye is excited by laser irradiation and emits fluorescence. Part of fluorescence emitted from each of droplets 604 is extracted through objective lens 608 onto a fluorescence detector side.

Objective lens 608 needs to capture fluorescence as efficiently as possible, and therefore preferably has a large numerical aperture (NA). In the first exemplary embodiment, for example, an objective lens with an NA of 0.85 is used. Fluorescence that has passed through objective lens 608 is passed through dichroic mirror 607. Then, fluorescence that has passed through dichroic mirror 607 is passed through optical filter 609 that transmits light with a fluorescence wavelength to remove light other than the fluorescence (e.g., leaked excitation light, and fluorescence emitted from other materials), and then fluorescence that has passed through optical filter 609 is collected through lens 610 into a fluorescence detector. When pinhole 611 with a size capable of transmitting only focused light is provided at a point where light is focused by lens 610, a stray light component can be cut off which is generated by reflection of laser light focused on the sensor chip from a region other than a focal position. Therefore, only fluorescence that has passed through the pinhole is input into fluorescence detector 612.

Fluorescence detector 612 needs to sensitively and quickly detect fluorescence whose intensity is about $1/10000$ to $1/100000$ of that of excitation light. Therefore, a high-sensitive detector such as a photomultiplier (PMT), an avalanche photodiode (APD), or a photodiode (PD) is used as fluorescence detector 612. Particularly, a PMT is preferred for its high sensitivity and high response speed. In the first exemplary embodiment, for example, a current output-type PMT is used.

<DNA Detecting Means>

DNA detecting means 208 determines a type of fluorescent probe solution contained in each of the sample droplets when a duration of detected fluorescence is a predetermined value. The duration of fluorescence refers to a time during which fluorescence having intensity equal to or higher than a threshold value is continuously detected.

More specifically, DNA detecting means 208 detects whether or not the DNA mixture contains a DNA to be detected based on transmitted light, a flow rate of the oil, and a flow rate of the mixture. The flow rate of the oil and the flow rate of the mixture correlate to the time during which each of the sample droplets flows through the ninth flow path. Therefore, DNA detecting means 208 specifies a flow rate of the mixture correlating to a detected duration with reference to a correlation between a flow rate of the mixture and a duration. DNA detecting means 208 detects whether each of the sample droplets contains a DNA to be detected by the fluorescent probe contained in the mixture whose flow rate has been specified. DNA detecting means 208 may be implemented by, for example, a computer including a CPU, a memory, a storage unit, an input-output unit, a display unit, and an interface.

DNA detection can be performed by the sensor chip and the DNA detection device which include the above components. The first exemplary embodiment will be specifically described with reference to a case where two target DNAs are tested by the sensor chip.

Testing two target DNAs means that target sequences are located in two positions. Therefore, different fluorescent probes are prepared which complementarily bind to these sequences, respectively. Each of the fluorescent probes can be artificially prepared to have a desired sequence. Each of the fluorescent probes is labeled with a fluorescent dye at one end and a quencher at the other end. In the first exemplary embodiment, two fluorescent probes are artificially prepared for two target DNAs, but both the fluorescent probes use a same fluorescent dye as a label. That is, the fluorescent probes are different in sequence, but are labeled with a same fluorescent dye. In the first exemplary embodiment, a fluorescent dye called fluorescein is used which has an excitation wavelength of 495 nm and a fluorescence wavelength of 520 nm. A fluorescent probe and a primer which are provided for one of the target DNAs are referred to as a first fluorescent probe and a first primer, respectively, and a fluorescent probe and a primer which are provided for the other target DNA are referred to as a second fluorescent probe and a second primer, respectively.

As shown in FIG. 3, in the mixture generating means, diluted DNA sample 302 and DNA polymerase 301 are mixed in a flow path, and then valve 306 is opened to mix the first fluorescent probe and the first primer with DNA sample 302 and DNA polymerase 301 in the flow path. During this period, valve 307 is kept closed to prevent the second fluorescent probe and the second primer from being mixed with the DNA sample. In such a state, mixture 305 containing the first fluorescent probe and the first primer is fed to the next one flow path that generates sample droplets to generate droplets. At this time, when a flow rate of each of pumps that feed the individual liquids is made constant to feed mixture 305 at a constant flow rate, droplets having almost a same size are generated in the one flow path that generates sample droplets. In this state, droplets each containing the first fluorescent probe and the first primer are generated so as to have a certain size (certain volume). Then, valve 306 is closed and valve 307 is then opened to mix the diluted DNA sample and the DNA polymerase with the second fluorescent probe and the second primer in the flow path to feed mixture 305 containing the second fluorescent probe and the second primer to the next one flow path that generates sample droplets. When a flow rate of the first fluorescent probe and the first primer and a flow rate of the second fluorescent probe and the second primer are made different from each other, a flow rate of mixture 305 output from the mixture generating means is different between when the first fluorescent probe and the first primer are fed and when the second fluorescent probe and the second primer are fed. Such a difference between a flow rate of the first fluorescent probe and the first primer and a flow rate of the second fluorescent probe and the second primer may be achieved by, for example, changing a pressure of each of the pump for feeding the first fluorescent probe and the first primer and the pump for feeding the second fluorescent probe and the second primer, or as shown in FIG. 3, changing a width, depth, and cross section of a flow path for feeding the first fluorescent probe and the first primer from those of a flow path for feeding the second fluorescent probe and the second primer without changing a pressure of each of the pumps.

Figure 7:
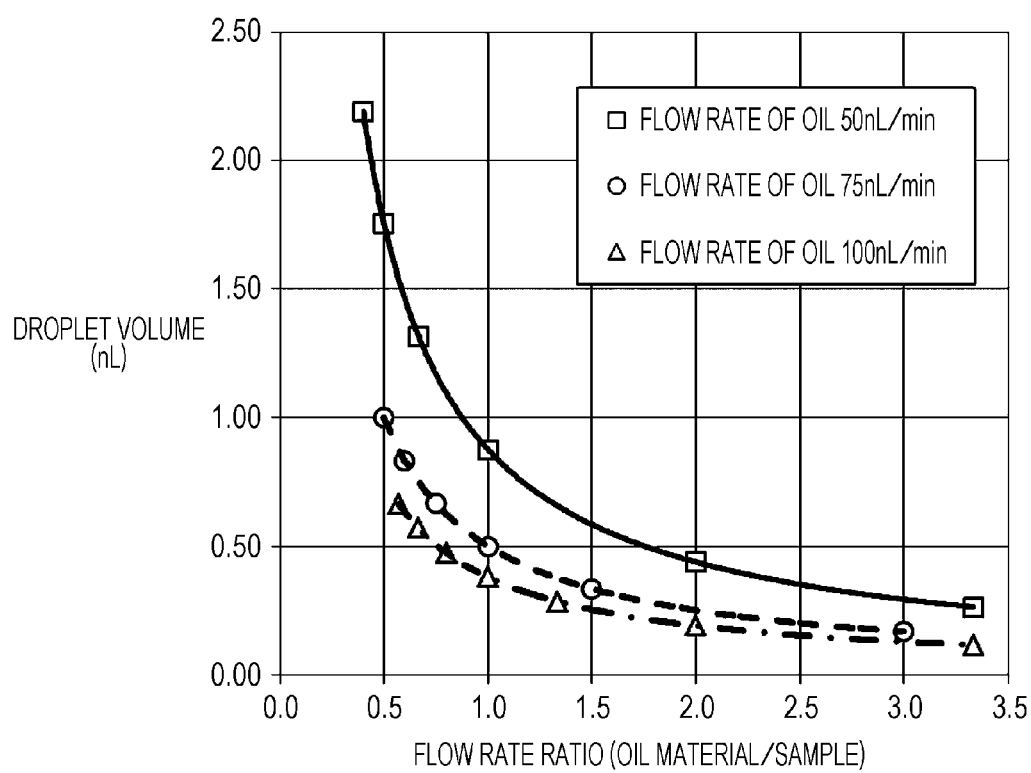
FIG. 7 is a graph showing a relationship between a flow rate ratio between a mixture and an oil material and a droplet volume when a flow rate of the oil is changed in the first exemplary embodiment.

FIG. 7 is a graph showing a relationship between a flow rate ratio between the mixture and the oil material and a droplet size when a flow rate of the oil is changed. This graph was experimentally obtained in the following manner. A flow rate of the oil material was fixed to 50 nL/min, 75 nL/min, and 100 nL/min, only a supply line of the first fluorescent probe and the first primer was activated, and a flow rate of the pump for feeding the first fluorescent probe and the first primer was changed stepwise. A horizontal axis represents a flow rate ratio between the oil material and the mixture, and a vertical axis represents an average volume of about 1000 droplets generated at each flow rate ratio. The average volume of generated droplets decreases as the flow rate ratio between the oil material and the mixture increases. From the result, it was confirmed that in the sensor chip according to the first exemplary embodiment, droplets having a volume of 0.1 to 2.2 nL were generated when a flow rate of the oil was in a range of 50 nL/min to 100 nL/min. Further, it was confirmed that droplets having any volume in the above range can be generated by changing a flow rate of the oil, a flow rate of the mixture, and a flow rate ratio between the oil and the mixture.

Figure 8:
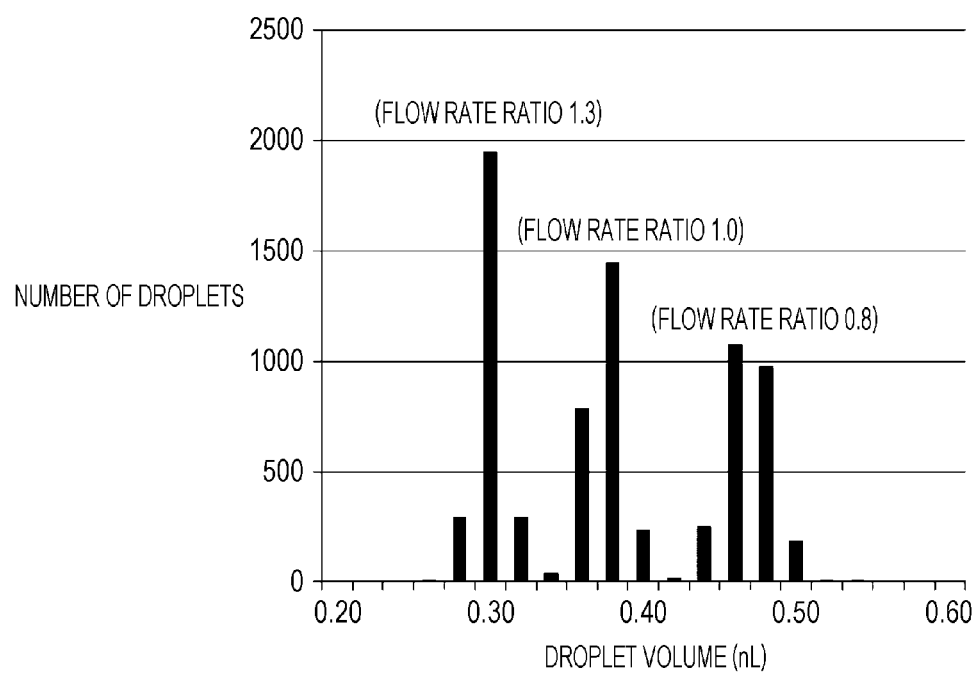
FIG. 8 is a graph of volume distribution of sample droplets generated when a flow rate ratio between the oil material and the mixture is changed in the first exemplary embodiment.

FIG. 8 is a graph of volume distribution of sample droplets generated when a flow rate ratio between the oil material and the mixture is changed. FIG. 8 is a distribution graph showing a relationship between a droplet volume and a number of droplets, which was obtained in the same manner as described above. That is, a flow rate of the oil material was fixed to 100 nL/min, only a supply line of the first fluorescent probe and the first primer was activated, and a volume distribution of droplets was determined by changing a flow rate of the mixture among 75 nL/min, 100 nL/min, and 125 nL/min. Under each of the above conditions, about 5000 droplets were generated in order. Under the condition where a flow rate of the mixture was 75 nL/min (flow rate ratio: 1.3), an average droplet volume was 0.3 nL, a maximum volume was 0.33 nL, a minimum volume was 0.26 nL, and variations were within ±0.03 nL (±3σ was calculated, where σ is a standard deviation). Under the condition where a flow rate of the mixture was 100 nL/min (flow rate ratio: 1.0), an average droplet volume was 0.38 nL, a maximum volume was 0.42 nL, a minimum volume was 0.34 nL, and variations were within ±0.04 nL. Under the condition where a flow rate of the mixture was 125 nL/min (flow rate ratio: 0.8), an average droplet volume was 0.48 nL, a maximum volume was 0.52 nL, a minimum volume was 0.42 nL, and variations were within ±0.05 nL. As can be seen from the results, a ratio between an average volume of a smallest droplet group of 0.3 nL and an average volume of a second smallest droplet group of 0.38 nL was 1.26, and a ratio between an average volume of the second smallest droplet group of 0.38 nL and an average volume of a third smallest droplet group of 0.48 nL was 1.26. As described above, when droplet groups are generated by changing a flow rate ratio between the oil material and the mixture so that their respective average droplet volumes increase by 25% or more in ascending order, size distributions of the different droplet groups are clearly separated as shown in FIG. 8. Therefore, the droplet groups generated under different conditions can be distinguished from each other based on a difference in size among them.

<DNA Detection Method>

Then, a method for detecting two target DNAs will be described which uses a first fluorescent probe and a first primer, and a second fluorescent probe and a second primer.

<Mixture Generating Step>

As shown in FIG. 3, the mixture generating means has a flow path that supplies the first fluorescent probe and the first primer and a flow path that supplies the second fluorescent probe and the second primer. These flow paths are provided separately from each other. Each of the flow paths has a valve provided at its outlet so that the first fluorescent probe and the first primer can be supplied separately from the second fluorescent probe and the second primer. Further, both the flow path that supplies the first fluorescent probe and the first primer and the flow path that supplies the second fluorescent probe and the second primer are designed to have a same depth of 30 μm, but are designed to have a different width. That is, the flow path for the first fluorescent probe has a width of 100 μm, and the flow path for the second fluorescent probe has a width of 120 μm. A pressure of a pump used to feed the first fluorescent probe and a pressure of a pump used to feed the second fluorescent probe are the same, and therefore a flow rate of an output from the mixture generating means varies depending on a difference in width between the flow paths that supply the fluorescent probes. In this case, the flow paths are different in width, but the same effects can be obtained also by changing their depth. That is, effects of the first exemplary embodiment are not affected as long as the flow paths can have different cross-sectional areas.

<Sample Droplet Generating Step>

First, valve 306 shown in FIG. 3 is opened to mix DNA polymerase 301, DNA sample 302, and first fluorescent probe and first primer 303 in a flow path to generate mixture 305, and mixture 305 is fed to next one flow path that generates sample droplets. At this time, a flow rate of mixture 305 at an outlet of the mixture generating means is, for example, about 100 nL/min. As shown in FIG. 4, mixture 305 is fed to input flow path 401 of the one flow path that generates sample droplets. In FIG. 4, a flow rate of oil material 402 in a flow path that supplies the oil material is set to about 100 nL/min. At this time, the mixture and the oil material join together at a T-shaped part formed by connecting input flow path 401 to the one flow path that generates sample droplets so that droplets of the mixture separated by the oil material are generated one after another as shown in FIG. 4. The DNA sample contained in the mixture is significantly diluted to adjust a number of DNA molecules per generated droplet to one or less. Under this condition, an average volume of the generated droplets is 0.38 nL. Then, the droplets are fed to the next DNA amplifying means.

Then, valve 306 shown in FIG. 3 is closed and valve 307 is opened to mix the DNA polymerase, the DNA sample, the second fluorescent probe and the second primer in the flow path to generate a mixture, and the mixture is fed to the next one flow path that generates sample droplets. At this time, a flow rate of the mixture at the outlet of the mixture generating means is about 125 nL/min. This results from the fact that the flow path that supplies the second fluorescent probe and the second primer is formed to have a width larger than that of the flow path that supplies the first fluorescent probe and the first primer, that is, the flow path that supplies the second fluorescent probe and the second primer has a larger cross-sectional area. As shown in FIG. 4, the mixture is fed to input flow path 401 of the one flow path that generates sample droplets. In FIG. 4, a flow rate of oil material 402 in the flow path that inputs the oil material is set to about 100 nL/min that is the same as that described above. At this time, the mixture and the oil material join together at the T-shaped part formed by connecting input flow path 401 to the one flow path that generates sample droplets so that droplets of the mixture separated by the oil material are generated one after another as shown in FIG. 4. The DNA sample contained in the mixture is significantly diluted to adjust a number of DNA molecules per generated droplet to one or less. Under this condition, an average volume of the generated droplets is 0.48 nL. Then, the droplets are fed to the next DNA amplifying means.

<DNA Amplifying Step>

The droplets containing the first fluorescent probe and the droplets containing the second fluorescent probe, which are generated in order, are fed to the DNA amplifying means such as one shown in FIG. 5 so that a DNA amplifying chamber is closely packed with the droplets. In FIG. 5, a number of droplets contained in the DNA chamber is small, but in the first exemplary embodiment, about 5000 droplets containing the first fluorescent probe and about 5000 droplets containing the second fluorescent probe are generated so that the DNA amplifying chamber is filled with a total of about 10000 droplets. Further, the mixture or the oil material contains a surfactant, and therefore coalescence of droplets does not occur even when the droplets are closely packed in the chamber or a thermal cycle is performed during DNA amplification. When a predetermined number of droplets are generated and the DNA amplifying chamber is filled with the droplets, valves provided at both the inlet and outlet of the DNA amplifying means are closed to perform DNA amplification.

The DNA amplification is performed using a fluorescent probe and a primer as illustrated in FIG. 10. In the first exemplary embodiment, two fluorescent probes and two primers are used for two target DNAs. However, these two fluorescent probes are prepared using a same fluorescent dye. Here, as described above, a fluorescent dye called fluorescein is used. The DNA amplification is performed by repeating a thermal cycle including a step of separating a double-stranded DNA into single-stranded DNAs, a step of hybridizing a fluorescent probe and a primer, and a step of extending a DNA from the primer. In the first exemplary embodiment, after the DNA amplifying means is filled with the droplets, the whole chamber is heated at 95° C. for about 5 minutes, and then a thermal cycle of 95° C. for 10 seconds, 65° C. for 10 seconds, and 75° C. for 10 seconds is repeated 40 times. In the DNA amplifying step, a DNA is amplified in the droplets containing a target DNA by a reaction between the target DNA and the fluorescent probe and the primer for the target DNA, and an amount of the fluorescent dye liberated in the droplets depends on a number of cycles of amplification. When the thermal cycle is repeated 40 times, one molecule of DNA in the droplets is amplified to the 40th power of 2, and therefore the fluorescent dye is liberated in an amount corresponding to the number of DNA molecules amplified. In droplets containing no target DNA, binding of the fluorescent probe does not occur due to the absence of target DNA, and therefore liberation of the fluorescent dye does not, of course, occur. It is to be noted that optimum conditions of the thermal cycle described above are different depending on types of fluorescent probe and primer used, and therefore temperature conditions are preferably set so as to be suitable for such materials. In the first exemplary embodiment, DNA amplification is performed under the above-described conditions, but its effects are not affected even when DNA amplification is performed by another method under different temperature conditions, as long as a DNA is normally amplified in the droplets containing a target DNA so that a function of the material that emits fluorescence as a result of DNA amplification can be activated. Further, a number of times of the thermal cycle is set to 40, but may be less than 40 as long as conditions are created where a sufficient fluorescence intensity can be obtained during subsequent fluorescence detection. An optimum number of times of the thermal cycle varies depending on a type of fluorescent probe or primer used, and therefore there is no particular problem even when a number of times of the thermal cycle is set to a value other than 40, as long as a DNA can be amplified to the extent that a sufficient fluorescence intensity can be obtained.

<Light Irradiation Step and Fluorescence Detection Step>

The droplets having been subjected to DNA amplification are introduced into the next optical waveguide means. In the first exemplary embodiment, the optical waveguide means is formed by bonding a glass plate having a thickness of 500 μm onto a Si substrate in which a groove having a width of 50 μm and a depth of 30 μm is formed. The droplets having been subjected to DNA amplification in the DNA amplifying means are fed through this flow path one after another in line. At this time, a feed rate of the droplets is always kept constant while the fluorescence detecting means counts a number of the droplets fed thereto. The number of the droplets is counted using the optical system shown in FIG. 6.

A semiconductor laser with 490 nm is used as the laser to excite fluorescein used as a fluorescent dye this time, and a high-sensitive and high-response current output-type PMT (photomultiplier) is used as the fluorescence detector. Further, a quartz objective lens with an NA (numerical aperture) of 0.85 is used as the objective lens to efficiently capture more fluorescence.

<DNA Detection Step>

An upper part of FIG. 1 is a schematic diagram showing droplets 102 and 103 flowing through flow path 101 of the optical waveguide means. A lower part of FIG. 1 is a graph showing optical signals of droplets 102 and 103, flowing through flow path 101 of the optical waveguide means shown in the upper part of FIG. 1, detected by a PMT. As shown in the upper part of FIG. 1, droplets 102 and 103 flow through flow path 101 of the optical waveguide means one after another in order. In the first exemplary embodiment, two types of droplets different in volume are generated using two fluorescent probes, and therefore four types of droplets flow through the flow path. The four types of droplets are: a small droplet having an average volume of 0.38 nL and containing the first fluorescent probe whose fluorescent dye has been liberated; a small droplet having an average volume of 0.38 nL and containing the first fluorescent probe whose fluorescent dye has not been liberated; a large droplet having an average volume of 0.48 nL and containing the second fluorescent probe whose fluorescent dye has been liberated; and a large droplet having an average volume of 0.48 nL and containing the second fluorescent probe whose fluorescent dye has not been liberated.

The optical system shown in FIG. 6 is used so that laser light is focused by objective lens 608 through glass plate 602 on one point in the flow path. The optical system used in the first exemplary embodiment is configured to obtain a beam diameter of about 0.7 μm in a focal position. The droplets flow through the flow path at a constant rate, and therefore the flowing droplets are individually irradiated with the laser light one by one to detect a signal of each of the droplets by the PMT. When the droplets flow through the flow path as shown in the upper part of FIG. 1, signals shown in the lower part of FIG. 1 are detected by the PMT. The droplets containing a target DNA emit fluorescence by laser irradiation, and therefore signals detected by the PMT have a high intensity. On the other hand, the droplets containing no target DNA do not emit fluorescence, and therefore signals detected by the PMT are very weak. Threshold value 105 for signal detection is set to a level at which signals of droplets that do not emit fluorescence can be detected so as to acquire a maximum signal intensity higher than the threshold value and a duration for which a detected signal is kept higher than the threshold value (which is referred to as crossing time).

The droplets containing the first fluorescent probe have a small average volume of 0.38 nL, and therefore a crossing time thereof is as short as A (sec) shown in the lower part of FIG. 1. The droplets containing the second fluorescent probe have a large average volume of 0.48 nL, and therefore a crossing time thereof is B (sec) longer than A. Therefore, even when a same fluorescent dye is used, two target DNAs can be distinguished based on a difference in crossing time. When a flow path configuration and droplet volumes are those described above, a difference in volume between droplets is almost equal to a difference in crossing time, and therefore an average of crossing time B is longer than an average of crossing time A by about 25%. In this way, the droplets containing the first fluorescent probe and the droplets containing the second fluorescent probe are distinguished based on the crossing time to count a number of the droplets containing the first fluorescent probe and a number of the droplets containing the second fluorescent probe.

Further, each of the droplets containing the first fluorescent probe is judged whether or not a target DNA is contained therein based on whether its maximum signal intensity during the crossing time is between threshold value 105 and threshold value 106 or is larger than threshold value 106. The same judgment is made on the droplets containing the second fluorescent probe.

Then, a ratio of a number of the droplets whose signal intensity is higher than threshold value 106 to a total number of the droplets containing the first fluorescent probe is determined. This makes it possible to quantitatively detect an amount of a target DNA contained in the original DNA sample. The same operation is performed on the droplets containing the second fluorescent probe, that is, a ratio of a number of the droplets whose signal intensity is higher than threshold value 106 to a total number of the droplets containing the second fluorescent probe is determined. This makes it possible to quantitatively detect an amount of a target DNA contained in the original DNA sample. It is to be noted that each of the droplets does not always contain a DNA, that is, a number of DNA molecules contained in each of the droplets is 1 or 0. Therefore, a quantitative value of a target DNA cannot be simply determined by division. For this reason, the quantitative value may be determined by statistical analysis according to the concept of Poisson distribution.

As described above, in the first exemplary embodiment, two target DNAs can be detected using a same fluorescent dye, and therefore the optical system for counting droplets is configured to detect only one fluorescence wavelength, which allows the optical system to have a very simple structure. Even when a number of target DNAs is three or more, the same effects can be obtained, that is, three or more targets can be quantitatively detected by a very simple optical system by preparing droplet groups for the different target DNAs so that average volumes of the groups are different by 25% or more from each other.

As has been described above, a size of sample droplets may be changed depending on a type of fluorescent probe used by creating conditions where, in the one flow path that generate sample droplets, a flow rate of the mixture is changed while a flow rate of the oil material is kept constant. On the other hand, a size of droplets may be changed by creating conditions where a flow rate of the oil material is changed while a flow rate of the mixture is kept constant.

Figure 11:
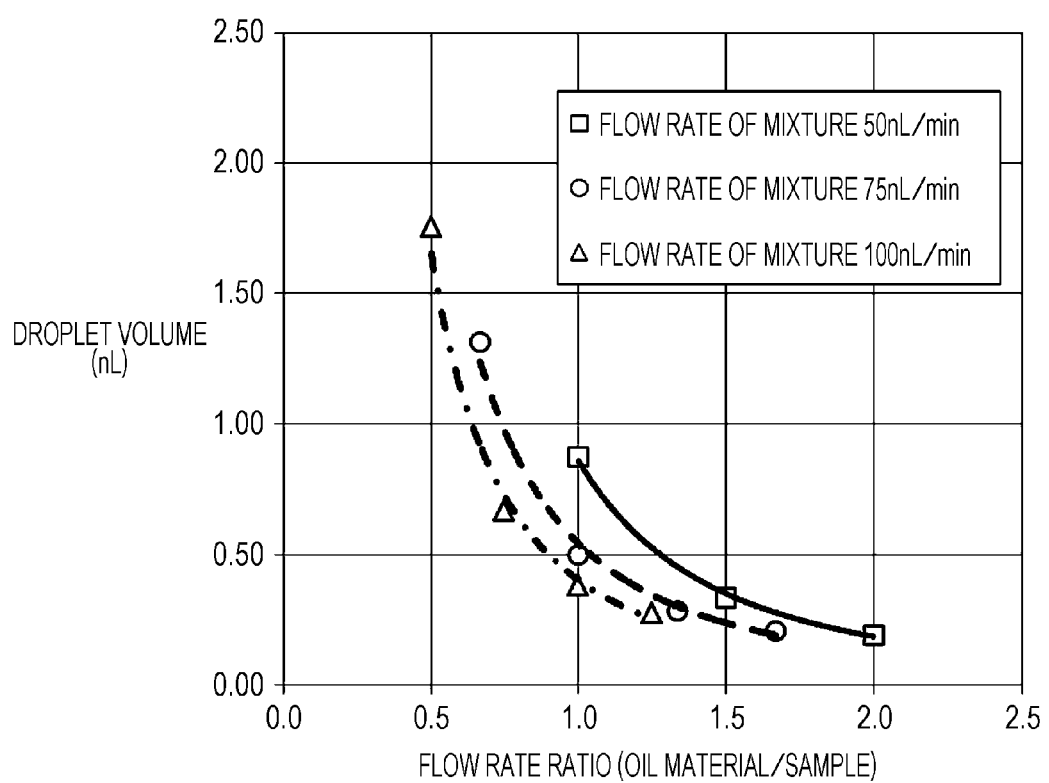
FIG. 11 is a graph showing a relationship between a flow rate ratio between the mixture and the oil material and a droplet volume when a flow rate of the mixture is changed in the first exemplary embodiment.

More specifically, a flow rate of the mixture is set to be constant both when the mixture containing the first fluorescent probe and the first primer is supplied and when the mixture containing the second fluorescent probe and the second primer is supplied. Under such conditions, a flow rate of the oil material when the mixture containing the first fluorescent probe and the first primer is supplied is made different from a flow rate of the oil material when the mixture containing the second fluorescent probe and the second primer is supplied. By doing so, a flow rate ratio between the mixture and the oil material is made different depending on a type of fluorescent probe used to generate sample droplets different in volume in the one flow path that generates sample droplets. FIG. 11 is a graph showing a relationship between a flow rate ratio between the mixture and the oil material and a droplet volume when a flow rate of the mixture is changed. FIG. 11 shows a relationship between a flow rate ratio between the mixture and the oil material and a volume of generated droplets when a flow rate of the oil material is changed while a flow rate of the mixture is fixed to 50 nL/min, 75 nL/min, and 100 nL/min. It was confirmed that an average droplet volume of a droplet group can be adjusted to any value in a range of 0.19 nL to 1.75 nL under the above test conditions. Therefore, a flow rate of the oil material may be changed so that average droplet volumes of droplet groups generated for different fluorescent probes are different by 25% or more from each other. Also in this case, the droplet groups can be distinguished from each other based on a difference in crossing time even when two or more different fluorescent probes use a same fluorescent dye.

Figure 9:
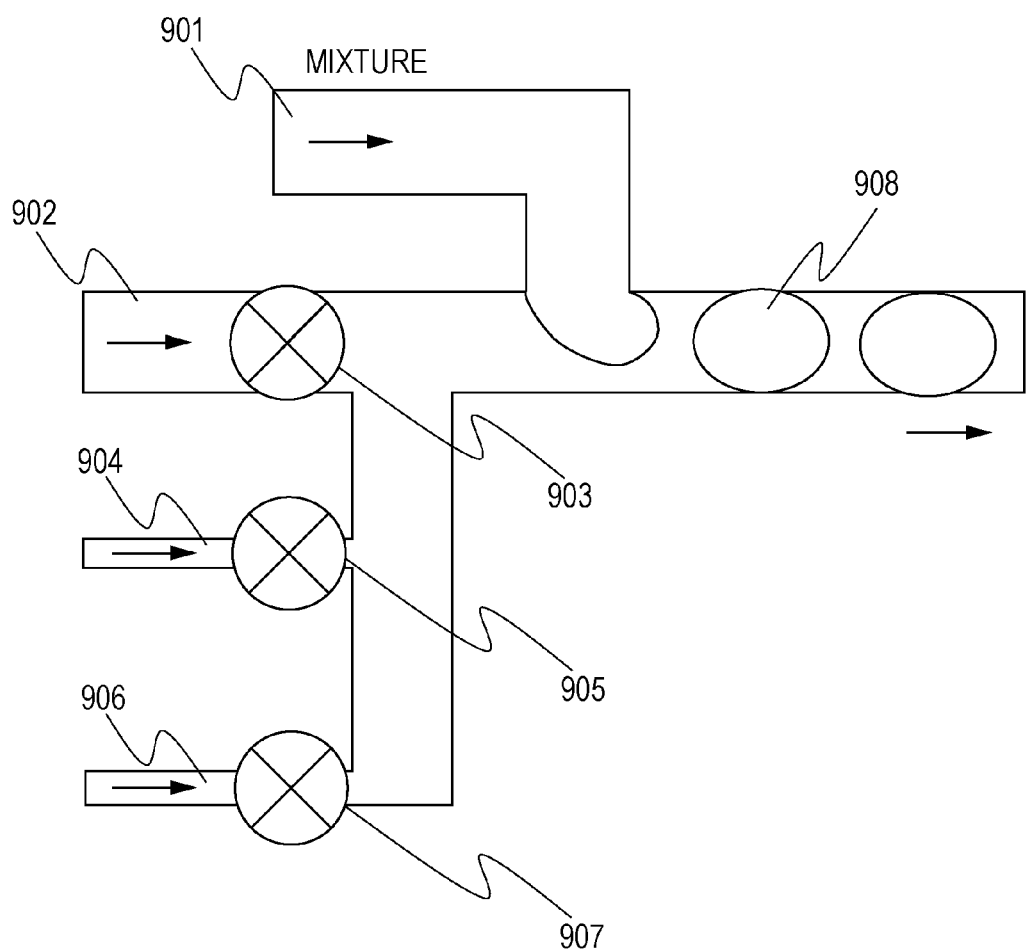
FIG. 9 is a schematic diagram showing a variation of the structure of the one flow path that generates sample droplets.

FIG. 9 is a schematic diagram showing a variation of the structure of the one flow path that generates sample droplets. In the one flow path that generates sample droplets, two or more flow paths that supply the oil material are provided, and valves are provided at their respective outlets so as to be independently opened and closed. For example, when the mixture containing the first fluorescent probe and the first primer flows, valves 903, 905, and 907 are all opened to achieve a high flow rate of the oil material at a junction where the mixture and the oil material join together. When the mixture containing the second fluorescent probe and the second primer flows, only valve 907 is closed to reduce the flow rate of the oil material, which makes it possible to achieve a different flow rate ratio between the mixture and the oil material and also to change a volume of generated droplets. In this way, the flow rate ratio may be changed by controlling the flow rate of the oil material, which is effective as long as volumes of droplets generated for different fluorescent probes are made different from each other by 25% or more. Here, the one flow path that generates sample droplets having such a flow path configuration as shown in FIG. 9 is used, but a flow path configuration thereof is not limited thereto as long as a flow rate of the oil material can be changed by a predetermined amount.

The DNA detection device according to the present disclosure is a microchannel device that quantitatively analyzes an amount of a target DNA in a collected sample such as blood. Particularly, the DNA detection device is useful when amounts of two or more target DNAs are simultaneously analyzed. According to the present disclosure, fluorescence detection can be achieved by an optical system having a very simple structure even when two or more DNAs are simultaneously analyzed. Therefore, the DNA detection device is particularly useful as a simple device that can be used for quick in-situ analysis in tailor-made medicine.

REFERENCE SINGS LIST

101 Flow path
102 Sample droplet containing no target DNA
103 Sample droplet containing target DNA
104 Fluorescently detected signal
105 Threshold value for signal detection
106 Second threshold value
201 Sensor chip
202 Mixture generating means
203 One flow path
204 DNA amplifying means
205 Optical waveguide means
206 Light source
207 Fluorescence detecting means
301 DNA polymerase
302 DNA sample
303 Solution containing first fluorescent probe and first primer
304 Solution containing second fluorescent probe and second primer
305 Mixture
306 Valve
307 Valve
401 Input flow path for mixture
402 Input flow path for oil material
403 Mixture
404 Oil material
405 Sample droplet
501 DNA amplification chamber
502 Sample droplet
503 Input flow path
504 Valve
505 Valve
506 Output flow path
507 Gap for separating DNA amplification chamber from surrounding members
601 Si substrate
602 Glass plate
603 Flow path
604 Droplet
605 Laser
606 Collimator lens
607 Dichroic mirror
608 Objective lens
609 Optical filter
610 Lens
611 Pinhole
612 PMT (photomultiplier)
901 Mixture
902 Oil material
903 Valve
904 Oil material
905 Valve
906 Oil material
907 Valve
908 Sample droplet
1001 Single-stranded DNA
1002 Single-stranded DNA
1003 Forward primer
1004 Reverse primer
1005 Probe
1006 Fluorescent dye
1007 Quencher

What is claimed is:

1. A DNA detection method comprising:
(a) placing a sensor chip in a DNA detection device, wherein
the DNA detection device comprises: a PCR processor, a fluorescence detector, and a DNA detector,
the sensor chip comprises: a first flow path, a second flow path, a third flow path, a fourth flow path, a fifth flow path, a sixth flow path, a seventh flow path, an eighth flow path, and a ninth flow path,
a first end of the first flow path and a first end of the second flow path are connected to a first end of the third flow path,
a second end of the third flow path is connected to a first end of the sixth flow path,
the fourth flow path and the fifth flow path are connected between the first end 15 and the second end of the third flow path, a second end of the sixth flow path and a first end of the seventh flow path are connected to a first end of the eighth flow path, a second end of the eighth flow path is connected to the PCR processor, and the PCR processor is connected to the ninth flow path;
(b) introducing an aqueous DNA solution and an aqueous DNA polymerase solution into the first flow path and the second flow path, respectively, to pass a first aqueous mixture of the aqueous DNA solution and the aqueous DNA polymerase solution through the third flow path, wherein the aqueous DNA solution contains target single-stranded DNA;
(c) introducing a first aqueous fluorescent probe solution obtained by mixing a first fluorescent probe with a first primer into the fourth flow path at a first flow rate during flowing of the first aqueous mixture through the third flow path to pass a second aqueous mixture of the first aqueous mixture and the first aqueous fluorescent probe solution through the sixth flow path, wherein the first fluorescent probe complementarily binds to a first single-stranded DNA of the target single-stranded DNA;
(d) introducing an oil material into the seventh flow path at a second flow rate to pass parts of the second aqueous mixture and parts of the oil material through the eighth flow path, wherein the parts of the second aqueous mixture and the parts of the oil material are arranged alternately along the eighth flow path;
(e) introducing a second aqueous fluorescent probe solution obtained by mixing a second fluorescent probe with a second primer into the fifth flow path at a third flow rate during flowing of the first aqueous mixture through the third flow path to flow a third aqueous mixture of the first aqueous mixture and the second aqueous fluorescent probe solution through the sixth flow path, wherein the second fluorescent probe is different from the first fluorescent probe and complementarily binds to a second single-stranded DNA of the target single-stranded DNA;

(f) introducing the oil material into the seventh flow path at a fourth flow rate to pass parts of the third aqueous mixture and parts of the oil material through the eighth flow path, wherein the parts of the third aqueous mixture and the parts of the oil material are arranged alternately along the eighth flow path;

(g) processing the parts of the second aqueous mixture and the parts of the third aqueous mixture by PCR with the PCR processor and then passing the parts through the ninth flow path;

(h) detecting, with the fluorescence detector, intensity of fluorescence output from each of the parts of the second aqueous mixture and the parts of the third aqueous mixture flowing through the ninth flow path; and (i) detecting, with the DNA detector, whether or not the target single-stranded DNA contains at least one selected from the first single-stranded DNA and the second single-stranded DNA based on the intensity of transmitted light, the first flow rate, the second flow rate, the third flow rate, and the fourth flow rate.

2. The DNA detection method according to claim 1, wherein in the step (i), the DNA detector
    acquires a duration for which the fluorescence detector continuously detects intensity of light equal to or higher than a first threshold value, and
    detects whether or not the target single-stranded DNA contained in the aqueous DNA solution contains the first single-stranded DNA or the second single-stranded DNA based on whether or not the duration is a time correlating to the first flow rate and the second flow rate or a time correlating to the third flow rate and the fourth flow rate.

3. The DNA detection method according to claim 2, wherein
    when the duration is the time correlating to the first flow rate and the second flow rate, the DNA detector determines that the target single-stranded DNA contains the first single-stranded DNA, and
    when the duration is the time correlating to the third flow rate and the fourth flow rate, the DNA detector determines that the target single-stranded DNA contains the second single-stranded DNA.

4. The DNA detection method according to claim 3, wherein
    the time correlating to the first flow rate and the second flow rate correlates to a flow rate of the parts of the second aqueous mixture in the ninth flow path, and
    the time correlating to the third flow rate and the fourth flow rate correlates to a flow rate of the parts of the third aqueous mixture in the ninth flow path.

5. The DNA detection method according to claim 1, wherein when the second flow rate and the fourth flow rate are the same and the first flow rate is different from the third flow rate, a flow rate ratio between the second aqueous mixture and the third aqueous mixture varies depending on a flow rate ratio between the first aqueous fluorescent probe solution and the second aqueous fluorescent probe solution.

6. The DNA detection method according to claim 5, wherein the first flow rate is different from the third flow rate due to a difference in cross-sectional area between the fourth flow path and the fifth flow path.

7. The DNA detection method according to claim 1, wherein the second flow rate and the fourth flow rate are different from each other.

8. The DNA detection method according to claim 1, wherein a fluorescent dye contained in the first aqueous fluorescent probe solution and a fluorescent dye contained in the second aqueous fluorescent probe solution emit fluorescence of a same wavelength.

9. The DNA detection method according to claim 1, wherein an average of volumes of the parts of the second aqueous mixture and an average of volumes of the parts of the third aqueous mixture are different by 25% or more.

* * * * *